United States Patent [19]

Lantzsch et al.

[11] Patent Number: 5,126,454
[45] Date of Patent: Jun. 30, 1992

[54] PROCESS FOR THE PREPARATION OF SULPHONYLISOUREAS

[75] Inventors: Reinhard Lantzsch, Wuppertal; Klaus-Helmut Müller, Duesseldorf; Martin Littmann, Cologne, all of Fed. Rep. of Germany

[73] Assignee: Bayer Aktiengesellschaft, Leverkusen, Fed. Rep. of Germany

[21] Appl. No.: 561,641

[22] Filed: Aug. 1, 1990

[30] Foreign Application Priority Data

Aug. 23, 1989 [DE] Fed. Rep. of Germany ....... 3927788

[51] Int. Cl.$^5$ ............................................. C07D 239/42
[52] U.S. Cl. .................................... 544/320; 544/321; 544/332
[58] Field of Search .................. 544/320, 321, 332

[56] References Cited

PUBLICATIONS

Hayashi et al., Chemical Abstracts, vol. 69, entry 59209c (1968).
Furukawa et al., Chemical Abstracts, vol. 78, entry 159566w (1973).
Chem. Pharm. Bull., 16(2), pp. 474–479 (1968).
Chem. Pharm. Bull., 21(3), pp. 478–482 (1973).

*Primary Examiner*—John M. Ford
*Attorney, Agent, or Firm*—Sprung Horn Kramer & Woods

[57] ABSTRACT

A process for the preparation of a sulphonylisourea of the formula

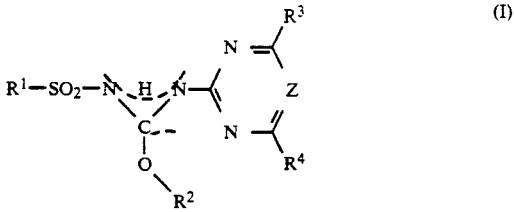
(I)

in which $R^1$ is an optionally substituted radical selected from the group consisting of alkyl, aralkyl, aryl and heteroaryl,
$R^2$ is alkyl or aralkyl,
$R^3$ is hydrogen, halogen or in each case optionally substituted alkyl or alkoxy,
$R^4$ is hydrogen, halogen or in each case optionally substituted alkyl or alkoxy and
Z is nitrogen or a CH grouping, which comprises reacting an isourea of the formula

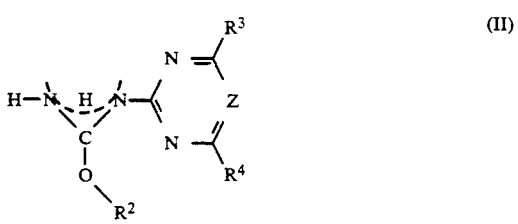
(II)

with a sulphonyl halide of the formula

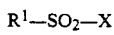
$R^1$—$SO_2$—X (III)

in which
X is halogen, in the presence of an acid acceptor at a temperature between about $-20°$ C. and $+50°$ C. Some of the compounds II are new.

4 Claims, No Drawings

PROCESS FOR THE PREPARATION OF SULPHONYLISOUREAS

The invention relates to a new process and new intermediates for the preparation of known herbicidally active sulphonylisoureas, and furthermore to a new process for the preparation of the intermediates (II).

It is known that certain sulphonylisoureas, such as, for example, N'-(4-methoxy-6-methyl-s-triazin-2-yl)-N''-(2-chloro-benzenesulphonyl)-O-methyl-isourea obtained when corresponding sulphonyl ureas, such as, for example, N'-(4-methoxy-6-methyl-s-triazin-2-yl)-N,,-(2-chloro-benzenesulphonyl)-urea, are reacted with triphenylphosphine and tetrachloromethane and—without intermediate isolation of the N-sulphonyl-imino-carbamoyl chlorides formed in this way additionally with alcohols, such as, for example, methanol, or alkoxides, such as, for example, sodium methoxide (compare EP-A 24,215). However, the sulphonylisoureas obtained in this way are strongly contaminated and require purification, for example by column chromatography.

Additionally, it is known that certain sulphonylisoureas, such as, for example, N-(2-chloro-benzene-sulphonyl)-imino-N'-(4,-methoxy-6'-methyl-triazinyl)-O-methyl-isourea, are obtained when corresponding N-sulphonylimino-thiocarbonic acid esters, such as, for example, O,S-dimethyl N-(2-chloro-benzenesulphonyl)iminothiocarbonate, are reacted with suitable amino compounds, such as, for example, 2-amino-4-methoxy-6-methyltriazine (compare CH-P 646,957). Apart from the fact that foul-smelling mercaptan is released in this process, the yields are also unsatisfactory.

It is furthermore known that certain sulphonylisoureas, such as, for example, N'-(4,6-dimethylpyrimidin-2-yl)-N,,-(2-chloro-benzenesulphonyl)-O-(1-methylethyl)-isourea, are obtained when suitable sulphonylguanidines, such as, for example, N,-(4,6-dimethyl-pyrimidin-2-yl)-N,,-methoxy-N,,,N,,,-bis(2-chloro-benzenesulphonyl)-guanidine, are reacted with alcohols, such as, for example, isopropanol (compare EP-A 173,311). However, the preparation of the sulphonylguanidines to be employed as starting materials in this case proceeds via a multistage synthesis route in often unsatisfactory yields.

It has now been found that sulphonylisoureas of the general formula (I)

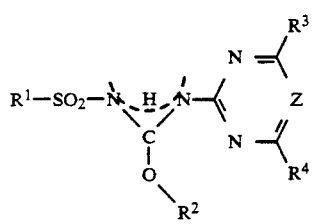

in which
R$^1$ represents an optionally substituted radical from the series comprising alkyl, aralkyl, aryl or heteroaryl,
R$^2$ represents alkyl or aralkyl,
R$^3$ represent hydrogen, halogen or in each case optionally substituted alkyl or alkoxy,
R$^4$ represents hydrogen, halogen or in each case optionally substituted alkyl or alkoxy and
Z represents nitrogen or a CH grouping, are obtained in good yields and in high purity, if isoureas of the general formula (II)

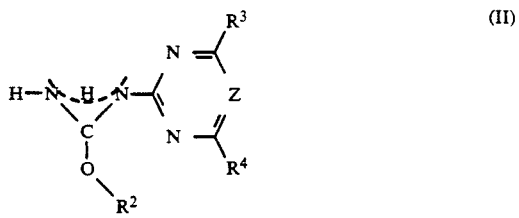

in which
R$^2$, R$^3$, R$^4$ and Z have the abovementioned meanings, are reacted with sulphonyl halides of the general formula (III)

$$R^1-SO_2-X \qquad (III)$$

in which
R$^1$ has the abovementioned meaning and
X represents halogen, in the presence of an acid acceptor and, if appropriate, in the presence of a diluent, at temperatures between $-20°$ C. and $+50°$ C.

It is to be regarded as surprising that the sulphonylisoureas of the formula (I) are obtained in good yields and in high purity from isoureas and sulphonyl halides by the process according to the invention, since it was known that, for example, structurally similar iminoethers (imido esters) form dealkylation products with sulphonyl chlorides (compare J. Chem. Soc. 1943, 101-104).

Advantages of the process according to the invention are, for example, that the required starting materials can be obtained in good yields in a few synthesis steps, using reasonably priced chemicals.

If, for example, 2-fluoro-benzenesulphonyl chloride and N-(4,6-dimethyl-pyrimidin-2-yl)-O-methyl-isourea are used as starting materials, the course of the reaction can be outlined by the following equation:

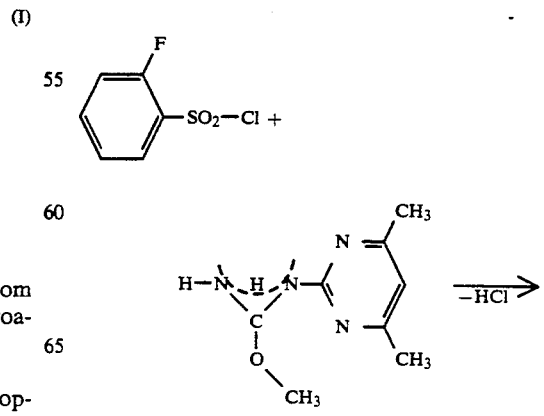

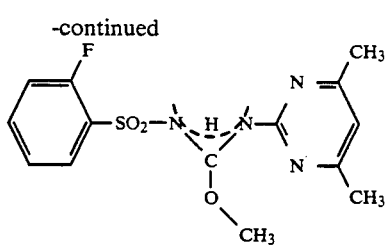

Formula (II) provides a general definition of the isoureas to be used as starting materials. Preferably, in formula (II)

$R^2$ represents $C_1$-$C_4$-alkyl or benzyl, $R^3$ represents hydrogen, fluorine, chlorine, bromine, $C_1$-$C_4$-alkyl, $C_1$-$C_4$-halogenoalkyl, $C_1$-$C_2$-alkoxy-$C_1$-$C_2$-alkyl, $C_1$-$C_4$-alkoxy, $C_1$-$C_4$-halogenoalkoxy or $C_1$-$C_2$-alkoxy-$C_1$-$C_2$-alkoxy, $R^4$ represents hydrogen, fluorine, chlorine, bromine, $C_1$-$C_4$-alkyl, $C_1$-$C_4$-halogenoalkyl, $C_1$-$C_2$-alkoxy-$C_1$-$C_2$-alkyl, $C_1$-$C_4$-alkoxy, $C_1$-$C_4$-halogenoalkoxy or $C_1$-$C_2$-alkoxy-$C'$-$Cz$-alkoxy-$C_1$-$C_2$-alkoxy, and Z represents nitrogen or a CH grouping Particularly preferred starting materials are the compounds of the formula (II) in which $R^2$ represents methyl or ethyl, $R^3$ represents chlorine, methyl, ethyl, trifluoromethyl, methoxymethyl, ethoxymethyl, methoxy, ethoxy or difluoromethoxy, $R^4$ represents chlorine, methyl, ethyl, trifluoromethyl, methoxy, ethoxy or difluoromethoxy, and Z represents a CH grouping.

Examples of the starting materials of the formula (II) which may be mentioned are: N-(4,6-dichloro-pyrimidin-2-vl)-, N-(4,6-dimethyl-pyrimidin-2-yl)-, N-(4-chloro-6-methyl-pyrimidin-2-N-(4,6-dimethoxy-pyrimidin-2-vl-)-, N-(4,6-diethoxypyrimidin-2-yl)-, N-(4-methoxy-6-methyl-pyrimidin-2-yl)-, N-(4-ethoxy-6-methyl-pyrimidin-2-yl)-, N-(4-ethyl-6-methoxy-pyrimidin-2-yl)-, N-(4-methoxy-6-trifluoromethylpyrimidin-2-yl)-, N-(4,6-bis-trifluoromethyl-pyrimidin2-yl)- and N-(4,6-bis-difluoromethoxy-pyrimidin-2-yl)-O-methyl-isourea The isoureas of the formula (II), with the exception of some N-(4,6-dimethyl-pyrimidin-2-yl)-O-alkyl-isoureas, are still unknown from the literature (compare Chem. Pharm. Bull. 21 (1973), 478–482).

The present invention also relates to new isoureas of the formula (IIa)

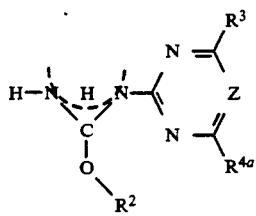

in which $R^2$ represents alkyl or aralkyl, $R^3$ represents hydrogen, halogen or in each case optionally substituted alkyl or alkoxy, $R^{4a}$ represents hydrogen, halogen or optionally substituted alkoxy and Z represents nitrogen or a CH grouping.

Preferred new isoureas are compounds of the formula (IIa) in which $R^2$ represents $C_1$-$C_4$-alkyl or benzyl, $R^3$ represents hydrogen, fluorine, chlorine, bromine, $C_1$-$C_4$-alkyl, $C_1$-$C_4$-halogenoalkyl, $C_1$-$C_2$-alkoxy-$C_1$-$C_2$-alkyl, $C_1$-$C_4$-alkoxy, $C_1$-$C_4$-halogenoalkoxy or $C_1$-$C_2$-alkoxy-$C'$-$Cz$-alkoxy-$C_1$-$C_2$-alkoxy, $R^{4a}$ represents hydrogen, fluorine, chlorine, bromine, $C_1$-$C_4$-alkyl, $C_1$-$C_4$-halogenoalkoxy or $C_1$-$C_2$-alkoxy-$C_1$-$C_2$-alkoxy and Z represents nitrogen or a CH grouping.

Particularly preferred new isoureas are compounds of the formula (IIa) in which $R^2$ represents methyl or ethyl, $R^3$ represents chlorine, methyl, ethyl, trifluoromethyl, methoxymethyl, ethoxymethyl, methoxy, ethoxy or difluoromethoxy, $R^{4a}$ represents chlorine, methoxy, ethoxy or difluoromethoxy and Z represents a CH grouping The compounds of the formula (II) or (IIa) are obtained by a new and inventive process when isoureas of the general formula (IV)

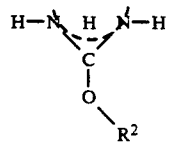 (IV)

in which $R^2$ has the abovementioned meaning,

—or acid adducts of compounds of the formula (IV-)—are reacted with azines of the general formula (V)

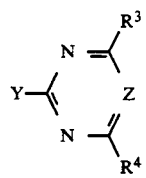 (V)

in which $R^3$ and $R^4$ have the abovementioned meanings,

Y represents halogen or alkylsulphonyl, and

Z represents nitrogen or a CH grouping, in the presence of an acid acceptor, such as, for example, potassium carbonate, and in the presence of a diluent, such as, for example, acetone, acetonitrile or dimethylformamide, at temperatures between 0° C. and 200° C., preferably between 10° C. and 150° C. (compare Preparation Examples).

The known N-(4,6-dimethyl-pyrimidin-2-yl)-O-alkyl-isoureas are obtained according to the literature (compare Chem. Pharm. Bull. 21 (1973), 478-482) by reaction of N-amidino-0-alkyl-isoureas with acetyl acetone. However, this synthesis method is only utilizable to a limited extent for the preparation of compounds of the formula (II). The process according to the invention for the preparation of compounds of the formula (II) from isoureas of the formula (IV) and azines of the formula (V) makes possible, in contrast, the preparation of a large number of new, otherwise unavailable compounds of the formula (II) in a simple manner and in surprisingly high yields. It is to be regarded as particularly surprising that even in the reaction of polyhalogenated azines, such as, for example, of 2,4,6-trichloropyrimidine, with isoureas of the formula (IV), the substitution reaction takes place virtually only in the 2-position with the formation of compounds of the formula (II) as, according to the literature, a uniform distribution of the 5 possible substitution products was to be expected (compare D. J. Brown, The Pyrimidines, p. 188-189, Interscience Publishers, John Wiley & Sons, New York-London, 1962).

The invention also relates to the two-step reaction sequence—first the reaction of isoureas of the formula (IV) with azines of the formula (V) and subsequently reaction of the isoureas of the formula (II) obtained in this way with sulphonyl halides of the formula (III).

Formula (IV) provides a general definition of the isoureas required as precursors. In formula (IV) $R^2$ preferably or in particular has that meaning which has already been indicated as preferred or as particularly preferred for Rz in the context of the description of the starting materials of the formula (II).

Examples of the starting materials of the formula (IV) which may be mentioned are: O-methyl-isourea and O-ethyl-isourea.

Preferred acid adducts of the compounds of the formula (IV) are their hydrogen sulphates or their sulphates.

The isoureas of the formula (IV) or their acid adducts are known organic synthetic chemicals.

Formula (V) provides a general definition of the azines furthermore required as precursors. In formula (V), $R^3$ and $R^4$ preferably or in particular have those meanings which have already been indicated as preferred or as particularly preferred for R: and R in the context of the description of the starting materials of the formula (II).

Y preferably represents chlorine or methylsulphonyl and Z represents nitrogen or a CH grouping.

Examples of the starting materials of the formula (V) which may be mentioned are: 2-chloro- and 2-methylsulphonyl-4,6-dichloro-pyrimidine, -4-chloro-6-methyl-pyrimidine, -4-chloro-6-methoxypyrimidine, -4,6-dimethoxy-pyrimidine, -4,6-diethoxypyrimidine, -4-methoxy-6-methyl-pyrimidine, -4-ethoxy-6-methyl-pyr -4-ethyl-6-methoxy-pyrimidine, methoxy-6-trifluoromethyl-pyrimidine, -4,6-bis-trifluoromethyl-pyrimidine, -4,6-bis-difluoromethoxy-pyrimidine and -4-methyl-6-difluoromethoxy-pyrimidine.

The azines of the formula (V) are known and/or can be prepared by processes which are known per se (compare J. Chem. Soc. 1957, 1830-1833; J. Org. Chem. 26 (1961), 792; U.S. Pat. No. 3,308,119 and U.S. Pat. No. 4,711,959).

The starting materials of the formula (II), in which $R^3$ and $R^4$ represent alkoxy, are preferably obtained in a synthesis sequence in which 2,4,6-trichloropyrimidine is reacted with an isourea of the formula (IV) —above —or an acid adduct thereof in the presence of an acid acceptor, such as, for example, sodium carbonate, potassium carbonate, calcium carbonate, triethylamine, pyridine, N,N-dimethylbenzylamine or N,N-dimethylcyclohexylamine, and in the presence of a diluent, such as, for example, toluene, xylene, methylcyclohexane, diisopropyl ether, tetrahydrofuran, dioxane, 1,2-dimethoxyethane, methyl tert-butyl ether or methyl tert-amyl ether, at temperatures between 0° C. and 200° C., preferably between 70° C. and 150° C., and the compounds of the formula (II) obtained in this case, in which $R^3$ and $R^4$ represent chlorine, are reacted with alkali metal alkoxides in the presence of the corresponding alcohols, at temperatures between 0° C. and 150° C., preferably between 10° C. and 100° C. (compare Example (II-2/II-3)).

Surprisingly, the reaction of N-(4,6-dichloropyrimidin-2-yl)-O-alkyl-isoureas with alkali metal alkoxides takes place to give N-(4,6-dialkoxy-pyrimidin2-yl)-O-alkyl-isoureas virtually quantitatively at moderately elevated temperatures (for example at the reflux temperature of methanol), whereas, for example, the reaction of 2-amino-4,6-dichloro-pyrimidine with sodium methoxide to give 4-amino-4,6-dimethoxy-pyrimidine has to be carried out at 140° C. to 150° C. (compare J. Chem. Soc. 1946, 81-85).

Formula (III) provides a general definition of the sulphonyl halides furthermore to be used as starting materials in the process according to the invention for the preparation of sulphonylisoureas of the formula (I). Preferably, in formula (III)

$R^1$ represents the radical

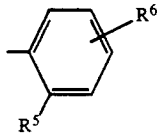

in which
$R^5$ represents hydrogen, halogen, cyano, nitro, $C_1$-$C_4$-alkyl (which is optionally substituted by halogen, cyano, $C_1$-$C_4$-alkoxy or $C_1$-$C_4$-alkoxycarbonyl), $C_1$-$C_4$-alkoxy (which is optionally substituted by halogen, cyano, $C_1$-$C_4$-alkoxy or $C_1$-$C_4$-alkoxy-carbonyl), $C_1$-$C_4$-alkylthio, $C_1$-$C_4$-alkylsulphinyl or $C_1$-$C_4$-alkylsulphonyl (which is optionally substituted by halogen, cyano, $C_1$-$C_4$-alkoxy or $C_1$-$C_4$-alkoxy-carbonyl), di-($C_1$-$C_4$-alkyl)-aminosulphonyl, N-($C_1$-$C_4$-alkoxy)-N-$C_1$-$C_4$-alkylaminosulphonyl, phenyl, phenoxy, $C_1$-$C_4$-alkoxy-carbonyl or di-($C_1$-$C_4$-alkylamino)-carbonyl and $R^6$ represents hydrogen or halogen, or, preferably, $R^1$ represents the radical

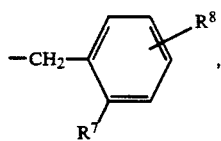

in which
$R^7$ represents hydrogen, halogen, cyano, nitro, $C_1$-$C_4$alkyl (which is optionally substituted by halogen, cyano, $C_1$-$C_4$-alkoxy or $C_1$-$C_4$-alkoxycarbonyl), $C_1$-$C_4$-alkoxy (which is optionally substituted by halogen, cyano, $C_1$-$C_4$-alkoxy or $C_1$-$C_4$-alkoxycarbonyl), $C_1$-$C_4$-alkylthio, $C_1$-$C_4$-alkylsulphinyl or $C_1$-$C_4$-alkylsulphonyl (which is optionally substituted by halogen, cyano, $C_1$-$C_4$-alkoxy or $C_1$-$C_4$-alkoxy-carbonyl), di-($C_1$-$C_4$-alkyl)-aminosulphonyl or $C_1$-$C_4$-alkoxy-carbonyl and $R^8$ represents hydrogen or halogen, or, preferably $R^1$ represents the radical

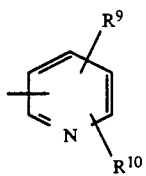

in which
R⁹ represents hydrogen, halogen, cyano, nitro, C₁-C₄-alkyl (which is optionally substituted by halogen), C₂-C₄-alkenyl (which is optionally substituted by halogen), C₁-C₄-alkoxy (which is optionally substituted by halogen), C₁-C₄-alkyl thio, C₁-C₄-alkylsulphinyl or C₁-C₄-alkylsul (which are optionally substituted by halogen), di-(C₁-C₄-alkyl)-aminosulphonyl, C₁-C₄-alkoxy-carbonyl, di-(C₁-C₄-alkyl)-aminocarbonyl or dioxolanyl and
R¹⁰ represents hydrogen or halogen, or, preferably
R¹ represents the radical

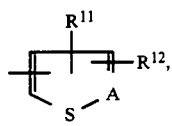

in which
A represents nitrogen or a CH grouping,
R¹¹ represents hydrogen, halogen, cyano, nitro, C₁-C₄-alkyl (which is optionally substituted by halogen, C₁-C₄-alkoxy or C₁-C₄-halogenoalkoxy), C₁-C₄-alkoxy (which is optionally substituted by halogen or C₁-C₄-alkoxy), C₁-C₄-alkylthio, C₁-C₄-alkylsulphinyl or C₁-C₄-alkylsulphonyl (which are optionally substituted by halogen), di-(C₁-C₄-alkyl)-aminosulphonyl or C₁-C₄-alkoxycarbonyl and
R¹² represents hydrogen or halogen, or, preferably
R¹ represents the radical

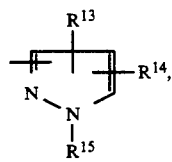

in which
R¹³ represents hydrogen, halogen, cyano, nitro, C₁-C₄-alkyl (which is optionally substituted by halogen), C₁-C₄-alkoxy (which is optionally substituted by halogen), dioxolanyl or C₁-C₄-alkoxy-carbonyl,
R¹⁴ represents hydrogen or halogen and
R¹⁵ represents hydrogen, C₁-C₄-alkyl, phenyl or (iso)quinolinyl
or, preferably
R¹ represents the radical

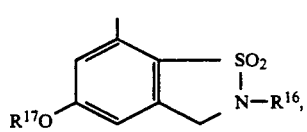

in which

R¹⁶ and R¹⁷ represent C₁-C₄-alkyl, or, preferably
R¹ represents the radical

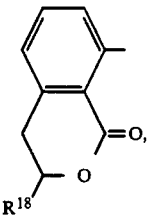

in which
R¹⁸ represents hydrogen or methyl, and
X preferably represents fluorine, chlorine or bromine.
Particularly preferred starting materials are the compounds of the formula (III), in which
R¹ represents the radical

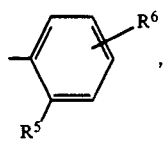

in which
R⁵ represents fluorine, chlorine, bromine, methyl, trifluoromethyl, methoxy, difluoromethoxy, trifluoromethoxy, methylthio, methylsulphonyl, dimethylaminosulphonyl, N-methoxy-N methylaminosulphonyl, phenyl, methoxycarbonyl or ethoxycarbonyl and
R⁶ represents hydrogen, fluorine or chlorine, or
R¹ represents the radical

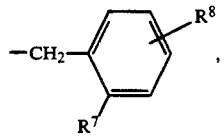

in which
R⁷ represents fluorine, chlorine, bromine, methyl, methoxy, ethoxy, difluoromethoxy, trifluoromethoxy, methoxycarbonyl or ethoxycarbonyl and
R⁸ represents hydrogen, or
R¹ represents the radical

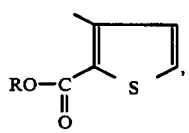

in which
R represents methyl or ethyl, or
R¹ represents the radical

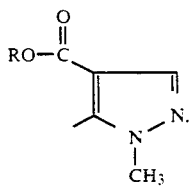

in which
R represents methyl or ethyl,
and in which in addition
X represents chlorine.

Examples of starting material of the formula (III) which may be mentioned are: 2-chloro-, 2,6-dichloro-, 2,5-dichloro-, 2-fluoro-, 2-bromo, 2-methyl-, 2-trifluoromethyl-, 2-methoxy-, 2-(2-methoxyethoxy)-, 2-metyylsulphonyl-, 2-chloro-6-methyl-, 2-bromo-6-methyyl-, 2-methylthio-, 2-trifluoromethylthio, 2-difluoromethylthio-, 2-phenoxy-, 2-difluoromethoxy-, 2-trifluoromethoxy-, 2-(2-chloroethoxy)-, 2-methylthiomethyl-, 2-dimethylaminosulphonyl-, 2-phenyl-, 2-methoxycarbonyl-, 2-ethoxycarbonyl-, 2-dimethylaminocarbonyl and 2-diethylaminocarbonyl-benzenesulpho chloride and (2-chloro-phenyl)-, (2-cyanophenyl)-, (2-methoxycarbonyl-phenyl)-, (2-trifluoromethoxy-phenyl) and (2-difluoromethoxy-phenyl)-methanesulphonyl chloride, furthermore 1-methyl-4-methoxycarbonyl-pyrazole-5-sulphonyl chloride, 1-methyl-4-ethoxycarbonyl-pyrazole-5-sulphonyl chloride, 2-methoxycarbonylthiophene-3-sulphonyl chloride, 3-trifluoromethylpyridine-2-sulphonyl chloride, 3-dimethylaminocarbonylpyridine-sulphonyl chloride, 3-dimethylaminocarbonyl-6-methyl-pyridine-2-sulphonyl chloride, 3-dimethylaminocarbonyl-6-chloro-pyridine-2-sulphonyl chloride and 1-(iso)quinolinyl-4-ethoxycarbonyl-pyrazole-5-sulphonyl chloride.

The sulphonyl halides of the formula (III) are known and/or can be prepared by methods which are known per se (compare J. Org. Chem. 33 (1968), 2104; J. Org. Chem. 25 (1960), 1824; DE-AS (German Published Specification) 2,308,262; EP-OS (European Published Specification) 23,140, 23,141, 23,422, 35,893, 48,143, 51,466, 64,322, 70,041, 44,808, and 44,809; U.S. Pat. Nos. 2,929,820, 4,282,242; 4,348,220 and 4,372,778 and also Angew. Chem. 93 (1981), 151).

The process according to the invention for the preparation of sulphonylisoureas of the formula (I) is carried out in the presence of an acid acceptor.

Acid acceptors which can be employed in the process according to the invention are all acid-binding agents customarily utilizable for reactions of this type. Those which are preferred are alkali metal hydroxides such as, for example, sodium hydroxide and potassium hydroxide, alkaline earth metal hydroxides such as, for example, calcium hydroxide, alkali metal carbonates and alkoxides such as sodium carbonate and potassium carbonates, sodium tert-butoxide and potassium tertbutoxide, furthermore aliphatic, aromatic or heterocyclic amines, for examples dicyclohexylamine, diisopropylamine, triethylamine, trimethylamine, tributylamine, dimethylaniline, dimethylbenzylamine, dimethylcyclohexylamine, pyridine, alkylated pyridines. such as 5-ethyl-2-methylpyridine, picolines, lutidines and collidines. furthermore, 1,5-diazabicyclo-[4.3.0]-non-5-ene (DBN), 1,8-diazabicyclo-[5.4.0]-undec-7-ene (DBU) and 1 cyclo-[2.2.2]-octane (DABCO).

The amines mentioned as acid acceptors, in particular dicyclohexylamine, are particularly preferred as acid-binding agents.

The process according to the invention for the preparation of the sulphonylureas of the formula (I) is preferably carried out using diluents Suitable diluents are virtually all inert organic solvents. These preferably include aliphatic and aromatic, optionally halogenated hydrocarbons such as pentane. hexane, heptane, cyclohexane, methylcyclohexane, petroleum ether, benzine, ligroin, decalin, benzene, toluene, xylene, methylene chloride, ethylene chloride, chloroform, carbon tetrachloride, chlorobenzene and o-dichlorobenzene, ethers such as diethyl ether, diisopropyl ether and dibutyl ether, methyl tert-butyl ether, methyl tert-amyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methylpyrrolidone and dimethyl sulphoxide, tetramethylene sulphone and hexamethylphosphoramide, furthermore also the abovementioned amines when they are employed as acid acceptors.

Preferred diluents for the process according to the invention are the abovementioned hydrocarbons and ethers.

The reaction temperatures can be varied within a relatively wide range in the process according to the invention. In general, the reaction is carried out at temperatures between $-20°$ C. and $+50°$ C., preferably at temperatures between $0°$ C. and $30°$ C.

The process according to the invention is in general carried out under normal pressure. However, it is also possible to work at elevated or reduced pressure (in general between 0.1 and 10 bar).

In order to carry out the process according to the invention, between 0.9 and 1.5 moles, preferably between 1.0 and 1.2 moles, of sulphonyl halide of the formula (III) and between 1 and 2 moles, preferably between 1.0 and 1.2 moles, of an acid acceptor are in general employed per mole of isourea of the formula (II).

In order to carry out the process according to the invention, the reaction components can be mixed in any sequence and, after completion of the reaction, worked up by customary methods.

In a preferred embodiment of the process according to the invention, the isourea of the formula (II) is stirred with an acid acceptor and, if appropriate, a diluent and the sulphonyl halide of the formula (III) is then slowly added with slight cooling. The reaction mixture is then stirred until the reaction is complete.

Working up can be carried out, for example, as follow: the reaction mixture is concentrated, the residue is stirred with water and the crystalline product is isolated by filtering off with suction. Further purification of the product can be carried out by washing with an organic solvent, such as, for example, toluene, or by recrystallization.

The sulphonylisoureas of the formula (I) which can be prepared by the process according to the invention can be used as herbicides (compare CH-P 646,957, EP-A 24,215, DE-OS (German Published Specification) 3,618,004).

PREPARATION EXAMPLES

Example 1

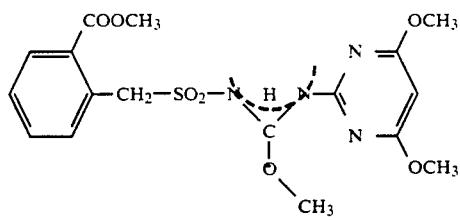

21.2 g (0.1 mol) of N-(4,6-dimethoxy-pyrimidin-2-yl)-0-methyl-isourea and 19.9 g (0.11 mol) of dicyclohexylamine are initially introduced in 100 ml of dimethoxyethane and 29.8 g (about 90% pure, 0.108 mol) of 2-methoxycarbonyl-benzylsulphonyl chloride, dissolved in 60 ml of dimethoxyethane, are added dropwise at 5 to 10° C. The mixture is allowed to come to room temperature and is subsequently stirred for 12 hours. After concentrating on a rotary evaporator, the residue is taken up in water, and the solution is stirred for 15 minutes and filtered off with suction. After thoroughly stirring with toluene and again filtering with suction, 36.3 g of white crystalline product are obtained, which contains 95% of N-(4,6-dimethoxy-pyrimidin-2-yl)-N'-(2-methoxycarbonyl-benzylsulphon-vl)-0-methyl-isourea. Yield: 82% of theory; melting point: 124°–126° C.

Starting materials of the formula (II)

Example (II-1)

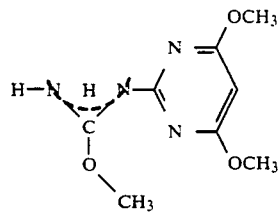

54.5 g (0.25 mol) of 2-methylsulphonyl-4,6-dimethoxy-pyrimidine, 69 g (0.5 mol) of potassium carbonate and 1500 ml of acetonitrile are mixed with stirring. 33.85 g (0.1375 mol) of O-methyl-isourea sulphate are then added and the mixture is heated to boiling for 17 hours. After cooling, the solution is filtered off with suction and the mother liquor is concentrated. After taking up the residue in methylene chloride, the solution is washed three times with water, dried and concentrated again. 49.9 g of N-(4,6-dimethoxy-pyrimidin-2-yl)-O-methylisourea are obtained in the form of yellow crystals of melting point 91°–95° C. (90% purity; yield 85% of theory).

Example (II-2)

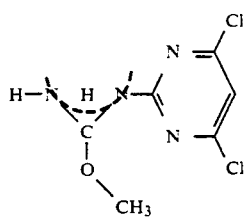

45.9 g (0.25 mol) of 2,4,6-trichloropyrimidine, 30.8 g (0.125 mol) of O-methyl-isourea sulphate and 51.8 g (0.375 mol) of ground potassium carbonate are suspended in 800 ml of toluene and stirred at 110° C. for 10 hours. After cooling, the crystalline solid is filtered off with suction, stirred with water for 15 minutes and again filtered off with suction. 39.4 g of N-(4,6-dichloro-pyrimidin-2-yl)-O-methylisourea are obtained (GC purity 98%: 38.6 g; yield: 69 of theory), melting point 178° C.

Example (II-3)

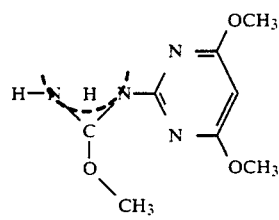

22.1 g (93.8% pure: 0.0938 mol) of N-(4,6-dichloro-pyrimidin-2-yl)-O-methyl-isourea are suspended in ml of methanol, and a solution of 13.5 g (0.25 mol) of sodium methoxide in 100 ml of methanol are added dropwise to this suspension. The reaction mixture is heated under reflux for 16 hours and then concentrated. The residue is taken up in water and extracted three times with methylene chloride. The solvent is removed from the combined extracts by distillation. 19.9 g (100% of theory) of N-(4,6-dimethoxy-pyrimidin-2yl)-0-methyl-isourea are obtained as a crystalline residue of melting point 98° C.

Example (II-4)

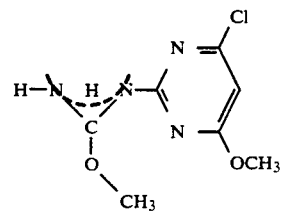

9.1 g (0.041 mol) of N-(4,6-dichloro-pyrimidin2-yl)-O-methyl-isourea are initially introduced in 80 ml of methanol. 2.2 g of sodium methoxide (0.041 mol), dissolved in 20 ml of methanol, are then added dropwise at 20° C. The mixture is subsequently stirred for 12 hours and concentrated, the residue is taken up in methylene chloride, and the solution is washed three times with water and concentrated again. 7.6 g (86% of theory) of N-(4-chloro-6-methoxy-pyrimidin-2-yl)    -O-methylisourea are obtained in the form of white crystals of melting point 118°-120° C.

The following are obtained analogously:

Example (II-5)

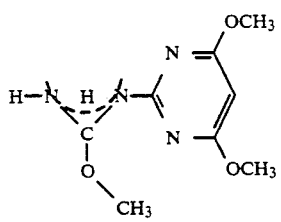

N-(4,6-dimethoxy-pyrimidin-2-yl)-O-ethyl-isourea
Yield: 72% (of theory); melting point: 96° C.

Example (II-6)

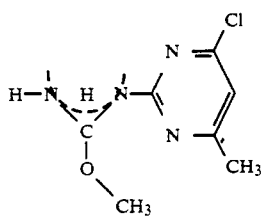

N-(4-chloro-6-methyl-pyrimidin-2-yl)-O-methyl-isourea; melting point 93° C.

Example (II-7)

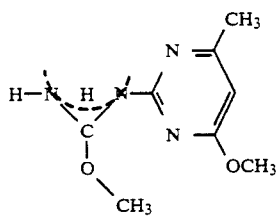

N-(4-methoxy-6-methyl-pyrimidin-2-yl)-O-methyl--isourea; melting point : 114° C.

Example 2

The following compound is obtained analogously to Example 1, likewise employing dicyclohexylamine as the base:

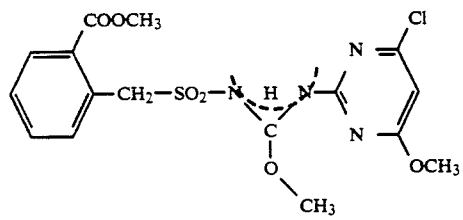

N-(4-chloro-6-methoxy-pyrimidin-2-yl)-N'-(2-methoxycarbonyl-benzylsulphonyl)-O-methyl-isourea.
Yield: 96% of theory; melting point: 128°-132° C.

Example 3

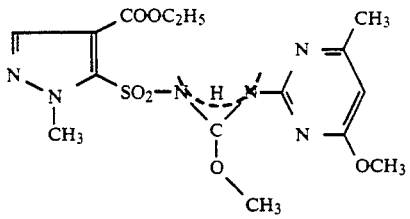

1.2 g (6.12 mmol) of N-(4-methyl-6-methoxy-pyrimidin-2-yl)-O-methyl-isourea and 0.9 g (6.7 mmol) of N,N-dimethyl-benzylamine are initially introduced in 10 ml of dimethoxyethane and 1.9 g (90% pure, 6.7 mmol) of (1-methyl-4-ethoxycarbonyl-pyrazol-5-yl)-sulphonyl chloride are added at 5° to 10° C. The reaction mixture is allowed to come to room temperature and is subsequently stirred for 10 hours. The solution is then concentrated, the residue is dissolved in methylene chloride, and this solution is washed three times with water. After drying and removal of the solvent by distillation, 2.1 g of a yellow oil are obtained, which contains 88% (according to HPLC) of the desired N-(4-methoxy-6-methyl-pyrimidin-2-yl)-N'-(1-methyl-4-ethoxycarbonyl-pyrazol-5-yl)-O-methyl-isourea.

Yield: 73% of theory.

$^1$H-NHR (CDCl$_3$): δ1,3 ppm (triplet, 3H) 2,45 ppm (s, 3H); 3,95 ppm (s, 3H); 3,975 ppm (s, 3H); 4,26 ppm (m, 3H+2H); 6,3 ppm (s, 1H); 7,8 ppm (s, 1H); 1,7 ppm (broad, NH ).

It is understood that the specification and examples are illustrative but not limitative of the present invention and that other embodiments within the spirit and scope of the invention will suggest themselves to those skilled in the art.

We claim:

1. An isourea of the formula

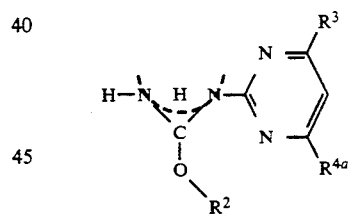

in which

R$^2$ is C$_1$-C$_4$-alkyl or benzyl,

R$^3$ is hydrogen, fluorine, chlorine, bromine, C$_1$-C$_4$-alkyl, C$_1$-C$_4$-halogenoalkyl, C$_1$-C$_2$-alkoxy-C$_1$-C$_2$-alkyl, C$_1$-C$_4$-alkoxy, C$_1$-C$_4$-halogenoalkoxy or C$_1$-C$_2$-alkoxy-C$_1$-C$_2$-alkoxy, and R$^{4a}$ is hydrogen, fluorine, chlorine, bromine, C$_1$-C$_4$-alkoxy, C$_1$-C$_4$-halogenoalkoxy or C$_1$-C$_2$-alkoxy-C$_1$-C$_2$-alkoxy.

2. An isourea according to claim 1, in which

R$^2$ is methyl or ethyl,

R$^3$ is chlorine, methyl, ethyl, trifluoromethyl, methoxymethyl, ethoxymethyl, methoxy, ethoxy or difluoromethoxy, and R$^{4a}$ is chlorine, methoxy, ethoxy or difluoromethoxy.

3. An isourea according to claim 2, in which R$^3$ is chlorine, methyl, ethyl, trifluoromethyl, methoxy, ethoxy or difluoromethoxy.

4. An isourea according to claim 2, in which R$^3$ is methoxy and R$^{4a}$ is methoxy.

* * * * *